United States Patent [19]

Fendler et al.

[11] Patent Number: 5,635,462
[45] Date of Patent: Jun. 3, 1997

[54] ANTIMICROBIAL CLEANSING COMPOSITIONS

[75] Inventors: Eleanor J. Fendler, Hudson; Ronald A. Williams, Stow; Demetrius A. Comes, Akron, all of Ohio

[73] Assignee: GOJO Industries, Inc., Cuyahoga Falls, Ohio

[21] Appl. No.: 550,278

[22] Filed: Oct. 30, 1995

Related U.S. Application Data

[63] Continuation of Ser. No. 273,108, Jul. 8, 1994, abandoned.
[51] Int. Cl.$^6$ ............... C11D 1/75; C11D 3/30; C11D 3/48
[52] U.S. Cl. ............ 510/131; 510/123; 510/132; 510/137; 510/138; 510/386; 510/518
[58] Field of Search .................. 510/123, 131, 510/132, 137, 138, 386, 518

[56] References Cited

U.S. PATENT DOCUMENTS

| | | | |
|---|---|---|---|
| Re. 28,778 | 4/1976 | Winicov et al. | 252/106 |
| 3,824,190 | 7/1974 | Winicov et al. | 252/106 |
| 3,862,151 | 1/1975 | Furia et al. | 260/270 R |
| 4,048,123 | 9/1977 | Hramachenko et al. | 252/545 |
| 4,329,334 | 5/1982 | Su et al. | 424/70 |
| 4,344,446 | 8/1982 | Erhardt | 132/7 |
| 4,626,529 | 12/1986 | Grollier | 514/159 |
| 4,632,772 | 12/1986 | Garabedian et al. | 252/106 |
| 4,835,148 | 5/1989 | Barford et al. | 514/179 |
| 4,883,659 | 11/1989 | Goodman et al. | 424/78 |
| 4,942,029 | 7/1990 | Scheps | 424/78 |
| 5,114,978 | 5/1992 | Corti et al. | 514/737 |
| 5,139,781 | 8/1992 | Birtwistle et al. | 424/401 |
| 5,244,666 | 9/1993 | Murley | 424/405 |
| 5,254,334 | 10/1993 | Ramirez et al. | 424/70 |
| 5,288,486 | 2/1994 | White | 424/78.08 |
| 5,306,504 | 4/1994 | Lorenz | 424/449 |
| 5,308,526 | 5/1994 | Dias et al. | 252/125 |

OTHER PUBLICATIONS

*The Antibacterial Activity of a New Chloroxylenol Preparation Containing Ethylenediamine Tetraacetic Acid*, A.D. Russell and J.R. Furr, Wales, 1977.

*The antibacterial activity of chloroxylenol in combination with ethylenediaminetetra–acetic acid*, J. Dankert and I.K. Schut, The Netherlands, 1975.

*Ethylene Diamine Tetra–acetic Acid and the Bactericidal Efficiency of Some Phenolic Disinfectants against Pseudomonas aeruginosa*, England, 1969.

*Sodium Hexametaphosphate in Emulsions of Dettol for Obstetric Use*, Edward Hatch, M.P.S. and Peter Cooper, Ph.C., 1948.

*The Action of Ethylenediaminetetra–acetic Acid on Pseudomonas aeruginosa*, G. W. Gray and S.G. Wilkinson, Yorkshire, England, 1964.

*The Effect of Ethylenediaminetetra–acetic Acid on the Cell Walls of Some Gram–Negative Bacteria*, B.W. Gray and S.G. Wilkinson, Great Britain, 1965.

*Acta Clinica Belgica*, J. Leguime and P.P. Lambert, 1969.

*A comparison of three commercially available antiseptics against opportunist Gram–negative pathogens*, H. Caplin and D.C. Chapman, Great Britain, 1976.

"Cut–off Effect in Antimicrobial Activity and in Membrane Perturbation Efficiency of the Homologous Series of N,N–Dimethylalkylamine Oxides" by Devinsky et al., *J. Pharm. Pharmacol.*, pp. 790–794, (1990).

*Primary Examiner*—Douglas J. McGinty
*Assistant Examiner*—Gregory R. Delcotto
*Attorney, Agent, or Firm*—Reese Taylor

[57] ABSTRACT

A cleansing composition includes a substituted phenol such as para-chloro-meta-xylenol, and at least one primary surfactant selected from the group consisting of amine oxides, phospholipids, partially neutralized carboxylic acids and diacids, betaines, ethoxylated methyglucosides, and mixtures thereof. The composition is devoid of conventional anionic and nonionic surfactants. Other additives such as viscosifiers or thickeners, emollients, fragrances, perfumes, coloring agents, and the like may also be added. The cleansing composition has been found to exhibit improved antibacterial properties while remaining mild on the skin.

19 Claims, No Drawings

ANTIMICROBIAL CLEANSING COMPOSITIONS

This application is a file wrapper continuation of U.S. patent application Ser. No. 273,108, filed Jul. 8, 1994, now abandoned.

TECHNICAL FIELD

This invention relates generally to cleansing compositions. More particularly, the present invention relates to antimicrobial cleansing compositions containing substituted phenols such as para-chloro-meta-xylenol (PCMX) as the active antimicrobial compound in the compositions. Specifically, the present invention relates to an antimicrobial cleansing composition containing substituted phenol, e.g., PCMX, and at least one primary surfactant selected from the group consisting of amine oxides, phospholipids, partially neutralized carboxylic acids and diacids, betaines, ethoxylated methylglucosides, and mixtures thereof. Notably, the antimicrobial cleansing compositions of the present invention are devoid of conventional surfactants such as most nonionic and anionic surfactants (fatty acid soaps, natural soap, etc.) and other substances commonly used therein (polyethylene glycol stearate, etc.) which have been found to inhibit the antimicrobial activity of the substituted phenol. Furthermore, the antimicrobial cleansing compositions do not require ethylenediaminetetraacetic acid (EDTA) or carriers or diluents.

BACKGROUND OF THE INVENTION

Antibacterial cleansing compositions are typically used to cleanse the arms and hands of the user and to destroy bacteria and any other microorganisms which might be present on the user's arms or hands. These compositions are widely used in the health care industry by hospital staff and other health care personnel as hand washing cleansers to prevent nosocomial infections. They are particularly suitable for use by hospital personnel such as surgeons, nurses and other health care professionals who might be subject to contact with bacteria and the like. They are also suitable for use by personnel in the food service and meat processing industries and, generally are used for antimicrobial cleansing of the hands and arms by the public.

There are several active antimicrobial agents currently available for use in cleansing compositions. For example, many antimicrobial cleansing compositions contain a bis-biguanide bacterial substance such as chlorhexidine digluconate (CHG). Other cleansing compositions use phenolic compounds. The antimicrobial activity of these substances, however, are often dependent upon the type(s) of surfactants or other ingredients employed therewith, and therefore, the use of the same ingredients with these antimicrobial substances will not necessary derive the same result. For instance, in pending U.S. patent application Ser. No. 246, 956 owned by the assignee of record, CHG is employed as the active antimicrobial agent. The cleansing compositions in that application include alkyl polyglucosides and non-ionic alcohol ethoxylates as the primary surfactants. However, in compositions containing substituted phenols such as PCMX as the active antimicrobial agent, most of the nonionic alcohol ethoxylates inhibit, rather than enhance, the antibacterial activity of the active agent.

Heretofore, antimicrobial cleansing compositions containing substituted phenols as the active antimicrobial agent have also included anionic detergents, soaps, surfactants, and the like, as well as other compounds (nonionic ethoxylated surfactants, polyethylene glycol etc.) which are known to substantially reduce the antibacterial activity of the phenolic compounds. For example, Winicov et al. U.S. Pat. No. 3,824,190 and its subsequent Reissue Pat. No. Re. 28,778 both disclose the use of substituted phenolic compounds and anionic, surface active detergents or soaps in an alcohol and water-based carrier. Additionally, chelating agents such as ethylenediaminetetraacetic acid (hereinafter, EDTA) were also added.

Similarly, Garabedian et al. U.S. Pat. No. 4,632,772 discloses an antimicrobial composition which is said to exhibit excellent mildness characteristics and which includes a substituted phenol, namely PCMX, an anionic detergent, a thickener such as ethylene glycol monostearate, and a foam builder such as a fatty acid alkanol amide. The thickener and fatty acid alkanol amides as well as the anionic surfactant hinder the antibacterial activity of the phenolic compound.

In addition, Corti et al. U.S. Pat. No. 5,114,978 discloses anhydrous blends of PCMX in surfactant mixtures. More particularly, White teaches a method for solubilizing PCMX in high concentrations of water or aqueous compositions. The compositions include PCMX, diethanolamides of fatty acids and anionic surfactants of the class diethanolammonium salts of alkylpolyoxyethylsulfuric acid. Again, anionic surfactants and fatty acid amides which have been reported to inhibit the antimicrobial activity of the phenolic compound are used in the composition.

Finally, White U.S. Pat. No. 5,288,486 relates to alcohol-based antimicrobial compositions including PCMX or CHG, hydropropyl cellulose, an alcohol, an emollient, and water. The use of alcohol as a solvent or carrier in the composition is known to defat the skin which may lead to skin dryness and irritation.

Substituted phenols and particularly, para-chloro-meta-xylenol (PCMX) have been used for decades in Europe and more recently in the United States as an active ingredient in antiseptics and hand washing agents for health care personnel. PCMX, also listed in the Merck Index as 4-chloro-3,5-dimethyl phenol, is a substituted phenol having the structure

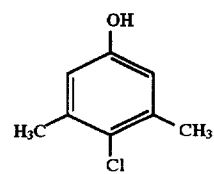

and is reported to have 60 times the antimicrobial activity of phenol against a wide spectrum of bacteria. Moreover, PCMX has been reported to yield high initial reductions of Gram-positive and Gram-negative bacteria as well as fungi, and also to provide good residual activity for several hours between hand washings.

Thus, the use of a substituted phenol such as PCMX as an active antimicrobial agent in a cleansing composition would appear to be well known. Typically, where PCMX is used in cleansing compositions, it is used in concentrations of from about 0.1 to 4 percent by weight. However, the majority of formulas contain 1 percent or less by weight.

Unfortunately, as discussed briefly hereinabove, like that of chlorohexidene digluconate (CHG), the efficacy of PCMX and other substituted phenols against microorganisms is highly dependent upon the carrier and other chemical constituents of the antimicrobial cleanser. For instance, it has been reported that the antimicrobial activity of PCMX is potentiated against *Pseudomonas aeruginosa* by the addition of the chelating agent ethylenediaminetetraacetic acid (EDTA) and/or the sequestering agent sodium hexametaphosphate, presumably due to bonding of the agents to metal ions in the cell wall. On the other hand, the antimicrobial activity of PCMX has been reported to be reduced in the presence of organic material, and may be inhibited by moderate concentrations of anionic surfactants. Antimicrobial activity is also lost as a consequence of reversible interactions between PCMX and noninonic surfactants, polyethylene glycol, and polyethylene glycol stearate. Similarly, reduction in the antibacterial efficacy of PCMX has also been found to be the direct result of its interaction with a variety of macromolecules, namely, methyl cellulose, polyethylene glycol 6000, and polysorbate 80. The importance of these chemical and biochemical interactions cannot be over-stated because they determine the biocidal effectiveness of PCMX in hand washing formulations and other antimicrobial products.

Accordingly, the need exists for an antibacterial composition containing a substituted phenol as the active antimicrobial ingredient therein, which is suitably effective for killing bacteria and other microorganisms, but which does not include conventional anionic surfactants or other chemical ingredients known to be detrimental to the antimicrobial activity of the substituted phenol. That is, the desired cleansing composition should include surfactants and carriers which do not significantly effect the antimicrobial activity of the substituted phenol.

SUMMARY OF INVENTION

It is therefore an object of the present invention to provide a cleansing composition which effectively kills bacteria and other microorganisms.

It is another object of the present invention to provide a cleansing composition, as above, which is devoid of conventional anionic surfactants.

It is still another object of the present invention to provide a cleansing composition, as above, which includes a substituted phenol such as PCMX and at least one primary surfactant.

At least one or more of the foregoing objects, together with the advantages thereof over the known art relating to antimicrobial cleansing compositions, which shall become apparent from the specification which follows, are accomplished by the invention as hereinafter described and claimed.

In general, the present invention provides an antimicrobial cleansing composition including a substituted phenol and at least one primary surfactant selected from the group consisting of amine oxides, phospholipids, partially neutralized carboxylic acids and diacids, betaines, ethoxylated methylglucosides, and mixtures thereof. The composition may also include viscosifiers, chelating and sequestering agents, emollients, humectants and other ingredients which do not materially affect the antimicrobial efficacy of the composition.

PREFERRED EMBODIMENT FOR CARRYING OUT THE INVENTION

The present invention is directed toward an antibacterial cleansing composition which effectively kills bacteria and other microorganisms, but is otherwise mild on the skin such that it does not cause skin irritation or dryness. That is, the antimicrobial cleansing compositions of the present invention have been found to reduce significantly the number of colony forming units (cfu's) of bacteria such as *Staphylococcus aureus* and the like and to do so without the use of any conventional anionic surfactants or other ingredients known to reduce the efficacy of the active antimicrobial agent employed therein.

The essential ingredients for such an antimicrobial cleansing composition generally includes a substituted phenol and at least one primary surfactant. These ingredients, along with other additives disclosed hereinbelow, provide compositions with excellent disinfecting properties as well as excellent cleansing properties.

As noted hereinabove and as is generally known in the art, the antibacterial activity for the compositions is generally provided by the substituted phenol found therein. Preferably, these substituted phenols are used in amounts ranging from about 0.1 to about 4 percent by weight of the total composition, with about 0.3 to 1 percent by weight of the total composition being most preferred. It will be appreciated, however, that more than 4 percent by weight of the antimicrobial agent may be employed without departing from the spirit of the invention, the upper limit being based solely upon the amount of substituted phenol which is considered to be non-toxic and non-irritating to the skin.

Any substituted phenol which is soluble in water or other non-alkanol solvent (triethylene glycol, propylene glycol, hexylene glycol etc.) may be used in the compositions of the present invention. Preferred substituted phenols include alkyl substituted, halogen substituted, phenol substituted, alkyl halo substituted, benzyl alkyl substituted, phenylethyl alkyl substituted and benzyl halo substituted phenols, and alkyl substituted, halogen substituted and alkyl halo substituted bisphenols, bis(hydroxyphenyl) alkanes, amino substituted phenols, resorcinol derivatives, trihydric phenol derivatives, naphthol derivatives and carboxylic acid substituted phenols (e.g., salicylic acid and esters). Most preferred of the substituted phenols is a chloro-substituted phenol, namely para-chloro-meta-xylenol (PCMX). As noted hereinabove, PCMX is reported to have 60 times the antimicrobial activity of phenol against a wide spectrum of bacteria. It has been reported to yield high initial reductions of Gram-positive and Gram-negative bacteria as well as fungi, and also to provide good residual activity for several hours between hand washings. It has also considered to be non-toxic and non-irritating to human skin at levels below about 3 percent by weight. In the samples presented hereinbelow, PCMX is the only substituted phenol employed therein. However, the present invention should not necessarily be limited to this particular substituted phenol as other such substituted phenols as noted hereinabove may also be suitable for the purposes of the present invention.

As noted hereinabove, at least one primary surfactant is also incorporated into the composition of the present invention. As used in this specification, the term "primary surfactant" means any surfactant which acts upon or in conjunction with the substituted phenol to enhance further, or at the least, to not reduce significantly, the antimicrobial activity of the substituted phenol. Accordingly, insofar as conventional anionic surfactants have been found to reduce substantially the antimicrobial activity of substituted phenols, they are not primary surfactants for purposes of this invention. Examples of conventional anionic surfactants generally include, but are not necessarily limited to, fatty acid soaps as well as sulfates, carboxylates, sulfonates, sulfosuccinates, phosphonates, phosphates, sarcosinates, and isethionates of hydrophobic moities. Moreover, as noted hereinabove, many nonionic surfactants also inhibit the antibacterial activity of substituted phenols. Accordingly, only the particular nonionic surfactants noted hereinbelow may be employed.

In order to overcome the problem of inhibition of the active antimicrobial ingredient, the composition of the present invention preferably includes primary surfactants selected from the group consisting of amine oxides, phospholipids, partially neutralized carboxylic acids and diacids, betaines, ethoxylated methylglucosides, and mixtures thereof. The amount of primary surfactant(s) to be added to the composition of the present invention is somewhat dependent upon the number of primary surfactants added. However, the amount of all of the primary surfactants together generally will not comprise more than about 20 percent by weight of the composition.

With respect to the amine oxides, any amine oxide may be employed, but preferably, an alkyl amine oxide is added to the composition in an amount ranging from 0 (absent) to about 10 percent by weight with about 5 to 7 percent by weight being most preferred. When the amine oxide is the sole primary surfactant employed in the composition, it is preferably added in amounts ranging from about 1 to about 10 percent by weight. Preferably, the amine oxide has a alkyl chain length of from about $C_8$ to about $C_{16}$, with chain lengths of from $C_{12}$ to $C_{14}$ being most preferred. Heretofore, the amine oxides were typically employed in cleansing formulations as secondary surfactants in conjunction with conventional anionic surfactants as the major or primary surfactant for cleaning and foam-enhancing purposes. While they are used for the same purposes in the present invention, it will be appreciated that they are no longer secondary surfactants. That is, the amine oxides of the present invention are generally the major surfactant in the composition. No conventional anionic surfactants are used.

The amine oxides used in the present invention are considered to be amphoteric surfactants. Examples of these amine oxides found to be suitable for the present invention include those available from McIntyre Chemical Co., Ltd. of Chicago, Ill., under the tradenames Mackamine LO (a $C_{12}$ alkyl amine oxide also known as lauramine oxide) and Mackamine CO (a $C_{12}$–$C_{14}$ alkyl amine oxide also known as cocamine oxide), as well as those available from Lonza, Inc., of Fair Lawn, N.J., under the tradenames Barlox 14 (a $C_{14}$ alkyl amine oxide) and Barlox 12 (a $C_{12}$ alkyl amine oxide). Furthermore, amidopropyl amine oxides such as those available from Henkel Corp. of Hoboken, N.J., under the tradenames Standamox LAO and Mackamine CAO may be employed.

In addition, alkylamides such as cocamide may be used in conjunction with the amine oxides or other primary surfactants to boost foaming and add to the viscosity of the composition. Preferred viscosity modifiers and foam stabilizers are the alkylamides which are also available from Henkel Corp. under the tradenames Standamide CD, Standamide SD, and Cocamide DEA.

These compounds are seen as being particularly effective in use with substituted phenols. That is, they do not significantly reduce the antibacterial activity of the substituted phenol and particularly have been found to be extremely effective with PCMX in killing *Staphylococcus aureus* and other microorganisms as detailed hereinbelow.

Other zwitterionic/amphoteric surfactants such as phospholipids and betaines may also be used in the compositions of the present invention. These surfactants are also considered to be primary surfactants as defined hereinabove and may be used in place of or in conjunction with the amine oxides noted hereinabove. When used, the phospholipids and betaines may be employed in amounts up to about 10 percent by weight.

One particular class of phospholipids suitable for use in the cleansing compositions of the present invention is alkyl phosphatidyl PG-dimonium chloride. The preferred alkyl phosphatidyl PG-dimonium chlorides are cocamidopropyl phosphatidyl PG-dimonium chloride, available from MONA Industries, Inc. of Paterson, N.J., under the tradename Phospholipid PTC; stearamidopropyl phosphatidyl PG-dimonium chloride, available from MONA under the tradename Phospholipid PTS; linoleamidopropyl phosphatidyl PG-dimonium chloride, available from MONA under the tradename Phospholipid EFA; and stearamidopropyl phosphatidyl PG-dimonium chloride/cetyl alcohol, available from MONA under the tradename Phospholipid SV. Preferably, such compounds are incorporated into the composition in an amount ranging from 0 (absent) to about 10 percent by weight of the total composition.

Additionally, betaines may also be used as the primary surfactant either alone or in conjunction with other primary surfactants identified herein. Preferably, up to 10 percent by weight of the total composition of an alkylammonio carboxylate having from 8 to 18 carbon atoms may be incorporated into the composition. One such alkylammonio carboxylate is cocobetaine, and is available from Mcintyre Chemical Co. of Chicago, Ill., under the tradename Mackam CB-35.

Still further, mixtures of partially neutralized carboxylic acids and diacids, e.g., sodium caproyl lactylate, may be employed as the primary surfactant. Preferably, such a compound is added to the cleansing composition in amounts ranging from 0 (absent) to about 5 percent by weight. At this point, it is noted that these partially neutralized carboxylic acids and diacids contain some anionic surfactants. However, such mixtures of these acid salts have considerable protonated acid character and therefore, are expressly excluded from the term "conventional anionic surfactants".

Notwithstanding the above surfactants, at least one type of nonionic surfactant, ethoxylated nonionic methylglucosides, may be used in the present invention. However, not all nonionic ethoxylates are suitable for this invention. In fact, the only ethoxylates known to date to maintain the desired anti-microbial activity of the substituted phenols are ethoxylated (10 moles) methylglucosides and ethoxylated (20 moles) methylglucosides. These ethoxylates may also be added in amounts ranging from 0 (absent) to about 10 percent by weight.

The composition may also include other additives such as thickeners, emollients, chelating and sequestering agents, fragrances, coloring agents, opacifying agents, pearlizing agents, vitamins and the like. For example, the composition may include a polymer viscosifier or thickener such as hydroxyethyl cellulose to make the composition more aesthetically pleasing. Examples of other suitable polymer viscosifiers include, but are not necessarily limited to, hydroxypropyl cellulose, methyl cellulose, and carboxymethyl cellulose.

A glycol may be added in order to quicken the rate of dissolution of the substituted phenol and as an emollient and/or humectant. Preferred glycols include propylene glycol, triethylene glycol, and hexylene glycol, with propylene glycol being most preferred. These glycols may be added in amounts ranging from 0 (absent) to about 10 percent by weight of the total composition, with about 3 percent being most preferred. Preferably, the PCMX or the substituted phenol is dissolved in at least a portion of the glycol prior to adding other ingredients to the solution. A 25 percent/75 percent ratio of PCMX to glycol is most preferred.

Still further, up to about 1 percent by weight of a chelating agent and/or sequestering agent may be added to soften the water-based composition. However, it will be appreciated that, like the other additives, these agents have no demonstrable effect on the antimicrobial activity of the substituted phenol compound employed. One example of a suitable chelating agent for the present invention is ethylenediaminetetra-acetic acid (EDTA). Most preferably, disodium EDTA is employed.

The composition of the present invention may further comprise minor but effective amounts of other conventional additives such as fragrances, color additives, opacifying agents, pearlizing agents, vitamins, etc. An example of a particular pearlizing agent includes, but is not necessarily limited to, ethylene glycol distearate. Generally, these additives are used in amounts which do not affect the essential nature of the composition with respect to its antimicrobial properties.

For optimal antibacterial efficacy, the pH of the composition should be between 4 and 8, and preferably between 5.5 and 6.5. To adjust the pH of the composition, any acid compatible with the components of the composition can be used. Preferred acids include lactic acid, citric acid, acetic acid, glycolic acid, and gluconic acid, with the first two acids being most preferred. Typically, less than 1 percent by weight of these acids are used to achieve the proper pH balance.

The balance of the composition is typically water so as to provide 100 percent by weight of the composition. Preferably, no alcohol-based solvent in used; although if alcohol is used, it would not materially affect the nature of the composition.

All percents by weight indicated herein are based upon the percent active composition. Thus, for example, where 5 percent by weight lauramine oxide is employed and the lauramine oxide is obtained from the manufacturer or has been diluted into solution so as to comprise a 30 percent active solution, 16.7 percent of the solution will have to be used in order to obtain the 5 percent by weight recommended.

The antimicrobial cleansing compositions of the present invention are generally prepared by dissolving substituted phenol, namely PCMX, in glycol as noted hereinabove, and adding this solution to one or more of the primary surfactant discussed hereinabove, in water. More particularly, the primary surfactant or surfactants, and other ingredients (fragrance, chelating agent, pearlizing agent, etc.) are added to the solution with stirring. The pH of the composition is adjusted with lactic acid or similar acid. The thickener/viscosifier is then preferably added and the solution is mixed until it is completely homogeneous. The pH is checked and adjusted again if necessary. This process may be employed with or without the application of heat to enhance hydration of the viscosifier, if required.

In order to demonstrate practice of the present invention, several antimicrobial cleansing compositions were prepared according to the concepts of the present invention as presented hereinabove and were tested to determine their effectiveness against at least one strain of the particular bacteria, Staphylococcus aureus. This particular strain is on deposit with and is available to the scientific public from the American Type Culture Collection (ATCC), Rockville, Md., under Accession No. 33591. The compositions of the present invention may, where indicated below, have also been studied with respect to other strains of bacteria also available to the scientific public from the ATCC under various Accession numbers. For instance, tests against at least one strain of *Serratia marcescens*, available to the scientific public from the ATCC under the Accession No. 14756, at least one strain of *Escherichia coli*, available to the scientific public from the ATCC under the Accession No. 8739, and at least one strain of *Pseudomonas aeruginosa*, available to the scientific public from the ATCC under Accession No. 15442, have also been conducted in some cases.

Initially, various prototype compositions were prepared from 0.5 percent by weight PCMX in a 35 percent diethylene glycol solvent solution, a noted percent by weight of a primary surfactant as detailed in Table I, and the balance, water. The pH of the composition was determined and adjusted to 7.0. The primary surfactants used included a variety of amine oxides including amidopropyl amine oxides, betaines, ethoxylated methylglucosides, mixtures of partially neutralized carboxylic acids and diacids and phospholipids. Also includes were a plurality of alkylamides. In addition, various compositions also included other conventional nonionic and anionic surfactants.

Each of the prototype compositions was then subjected to a thirty-second kill study of the challenge bacteria, *Staphylococcus aureus* (ATCC Accession No. 33591) and *Escherichia coli* (Accession No. 8739). For this study, lyophilized vials of *Staphylococcus aureus* (ATCC Accession No. 33591) and *Escherichia coli* (ATCC Accession No. 8739) were obtained. Forty eight hours prior to performing the efficacy study, each vial of bacteria was rehydrated into a bottle of tryptic soy broth (TBS), and incubated at about 35° C. for between 20 and 28 hours (about 24 hours). Two TSA plates were streaked for isolation and incubated at the same temperature for about 24 hours. Immediately prior to performing the efficacy protocol, a bacterial suspension was prepared to a concentration of approximately $1 \times 10^9$ cfu's/ml by swabbing the plate culture and suspending the bacteria into a sterile test tube containing 10 ml sterile physiological saline.

Ten milliliter samples of the test solutions were then placed into sterile 30 ml beakers containing a magnetic sir bar. The beaker with the test sample was placed onto a magnetic stirrer and approximately 10 to 15 seconds prior to inoculating the test sample with the challenge bacteria, the stirrer was turned on to allow good mixing without addition of air into the sample. One hundred microliters (µl) of challenge bacteria were introduced into the sample at time 0 and allowed to mix for approximately 20 seconds. Two hundred-fifty µl of the challenged sample was removed with a 250 µl positive displacement pipettor and dispensed at 30 seconds into 24.74 ml of neutralizing broth (2 percent tryptic soy broth (TSB), 10 percent Polysorbate 80, 4 percent Polysorbate 20, 0.75 percent Lecithin, 0.5 percent Dextrose, and 82.75 percent Distilled Water) and mixed well. Serial dilutions were made by standard methods well known in the art and plated into pour plates with tryptic soy agar (TSA) containing Polysorbate 80 and Lecithin (available from BBL). The plates were incubated at 35° C. for 48 hours and plates containing 30–300 colonies were counted. The challenge bacterial suspension was enumerated as were the test solutions using 10 ml of Sterile Physiological Saline as the test solution.

The test results were used to determine which surfactants could be used in formulations of the present invention. Table I, presented hereinbelow, shows the efficacy of reduction of colony forming units (cfu's) of *Escherichia coli* (ATCC Accession No. 8739) and *Staphylococcus aureus* (ATCC Accession No. 33591), respectively, for several compositions having various surfactants in water with 0.5 percent by weight PCMX. The efficacy results have been calculated on a log scale in order to provide a better understanding of the significant improvement in effectiveness on bacteria certain surfactants have as compared to other surfactants. In percentages, efficacy is considerably less clear insofar as many of these compositions reduce the number of cfu's by greater than 99 percent (a 2 log reduction).

TABLE I

CHLOROXYLENOL/SURFACTANT EFFICACY STUDY
THIRTY SECOND KILL STUDY AGAINST
*Escherichia coli* AND *Staphylococcus aureus*

| INGREDIENTS (supplier) | REDUCTION LOG | |
| --- | --- | --- |
| | *Escherichia coli* (ATCC 8739) | *Staphylococcus aureus* (ATCC 33591) |
| Lauramine oxide (McIntyre) | | |
| 2% | >5.2889 | >5.3222 |
| 5% | >5.127 | >5.2028 |
| 6% | >5.2889 | >5.3222 |
| Lauramine oxide (Henkel) | | |
| 2% | >5.127 | >5.2028 |
| 6% | >5.127 | >5.2028 |
| Cocamidopropyl phosphatidyl PG-dimonium chloride | | |
| 6% | >5.2889 | >5.3222 |
| Ethoxylated (10 moles) methylglucoside | | |
| 6% | >5.2889 | >5.2889 |
| Sodium capryl lactylate | | |
| 2% | >5.2889 | >5.3222 |
| 6% | 4.4438 | 4.3010 |
| Cocobetaine | | |
| 5% | >5.127 | >5.2028 |
| Cocamine oxide | | |
| 2% | >5.127 | >5.2028 |
| 6% | >5.127 | >5.2028 |
| $C_{14}$ alkyl amine oxide | | |
| 2% | >5.127 | >5.2028 |
| 6% | >5.127 | >5.2028 |
| $C_{12}$ alkyl amine oxide | | |
| 2% | >5.127 | >5.2028 |
| 6% | >5.127 | >5.2028 |
| Cocamidopropyl amine oxide | | |
| 2% | >5.127 | >5.127 |
| Capramide DEA | | |
| .5% | >5.127 | >5.2028 |
| 2% | >5.127 | >5.2028 |
| Cocamide DEA (Henkel) | | |
| .5% | >5.127 | >5.2028 |
| 2% | >5.127 | >5.2028 |
| Cocamide DEA (McIntyre) | | |
| .5% | >5.127 | 4.6587 |
| Polyoxyethylene (10) tridecanol | | |
| 2% | <1.2028 | 3.9510 |
| 6% | <1.2028 | 2.9733 |

TABLE I-continued

CHLOROXYLENOL/SURFACTANT EFFICACY STUDY
THIRTY SECOND KILL STUDY AGAINST
*Escherichia coli* AND *Staphylococcus aureus*

| INGREDIENTS (supplier) | REDUCTION LOG | |
| --- | --- | --- |
| | *Escherichia coli* (ATCC 8739) | *Staphylococcus aureus* (ATCC 33591) |
| Polyoxyethylene (8) Linear $C_{9-11}$ alkanol | | |
| 2% | <1.2028 | >5.127 |
| 6% | <1.2028 | >5.127 |
| Disodium oleamido MEA sulfosuccinate | | |
| 2% | <1.3222 | ≈1.5646 |
| 6% | <1.3222 | <1.2889 |
| Disodium dimethicone copoylol sulfosuccinate | | |
| 2% | <1.3222 | <5.2889 |
| 6% | <1.3222 | <1.5107 |
| $C_{14-16}$ alpha olefin sulfonate | | |
| 2% | <1.3222 | <1.2889 |
| 6% | <1.3222 | <1.2889 |
| Sodium laureth-3 sulfate | | |
| 2% | <1.3222 | <1.2889 |
| 6% | <1.3222 | <1.2889 |
| Cocamphodiacetate | | |
| 2% | <1.3222 | >5.2889 |
| 6% | <1.3222 | <1.5899 |
| Disodium oleamido PEG-2 sulfosuccinate | | |
| 2% | <1.3222 | <1.2889 |
| 6% | <1.3222 | <1.2889 |
| Sodium lauryl sarcosinate | | |
| 2% | 4.1919 | 2.1275 |
| 6% | 3.3422 | <1.5899 |
| Sodium cocoyl sarcosinate | | |
| 2% | 2.6365 | 2.9465 |
| 6% | 1.7245 | <1.2889 |
| Laureth-5 carboxylic acid | | |
| 2% | <1.3222 | <1.2889 |
| 6% | <1.3222 | <1.2889 |
| Alkyl polyglucoside 200 (Henkel) | | |
| 2% | 2.4691 | <1.4886 |
| 6% | <1.2095 | <1.4886 |
| Alkyl polyglucoside 400 (Henkel) | | |
| 2% | <1.2095 | <1.4886 |
| 6% | <1.2095 | <1.4886 |
| Alkyl polyglucoside 600 (Henkel) | | |
| 2% | <1.2095 | <1.4886 |
| 6% | <1.2095 | <1.4886 |
| Alkyl polyglucoside (Seppic) | | |
| 2% | >5.2095 | <1.4886 |
| 6% | <1.2095 | <1.4886 |

As shown in Table I, only those surfactants discussed hereinabove, i.e., amine oxides, phospholipids, partially neutralized carboxylic acid and diacids (sodium capryl lactylate), betaines, and ethoxylated methylglucosides do not reduce the antibacterial activity of PCMX. In contrast, nonionic ethoxylates other than the other ethoxylated methylglucosides, and other nonionic and anionic surfactants listed in Table I are shown to reduce significantly the antibacterial activity of PCMX. In fact, each of the surfactants not provided for hereinabove shows a log reduction value of less than 3, while those noted hereinabove all have a log reduction value of at least 4 and, in most instances, of at least 5. Thus, it is believed evident that the primary surfactants of the present invention do not contribute to the inhibition of the antimicrobial activity of the substituted phenols and, in some instances, may even enhance the activity of the antimicrobial agent employed.

Next, six more prototype Compositions (1 through 6, inclusive) were prepared using all of the essential ingredients of the present invention and according to the present invention as detailed hereinabove. Specifically, the compositions included differing amounts of a substituted phenol, namely PCMX (about 0.3, 0.5 and 1 percent by weight, respectively); about 5 or 7 percent by weight of a primary surfactant, namely lauramine oxide, about 3 or 6 percent by weight of propylene glycol; and about 0.7 percent by weight hydroxyethyl cellulose. The pH of each of the first three compositions was adjusted to about 5.5 with lactic acid while the latter three compositions were adjusted to a pH of about 7.

Table II presents the compositional formulations of each of the compositions 1 through 6 and Table III reports the efficacy in terms of log reduction for a thirty-second kill study preformed against Staphylococcus aureus (ATCC Accession No. 33591) and, in the case of the first three compositions, also against Escherichia coli (Accession No. 8739), *Pseudomonas aeruginosa* (ATCC Accession No. 15442), and *Serratia marcescens* (ATCC Accession No. 14756).

As can be seen from Table II and III, the amount of PCMX employed (from about 0.3 to 1 percent by weight) and the amount of primary surfactant employed (from about 5 to 7 percent by weight) had little effect upon the antimicrobial activity of the PCMX. Moreover, the change in pH of the compositions (from about 5.5 to 7) also had little effect on the efficacy of the bacterial kill of the composition. The fact that small amounts of PCMX can be used to obtain essentially the same efficacy in reduction of bacteria as larger amounts of PCMX in compositions containing essentially the same ingredients is seen as a significant improvement over the antimicrobial soap art.

In the next study, the in vitro antimicrobial efficacy of several commercially available PCMX antimicrobial skin cleansers are evaluated and compared to two of the prototype PCMX compositions of the present invention, which were formulated utilizing ingredients having positive synergies with PCMX as presented hereinabove. More particularly, ten professional antimicrobial lotion soaps were obtained from local medical distributors, while two antimicrobial soap formulations of the present invention were prepared in the laboratory of the assignee of record. While the exact compositional amounts of the commercially available antimicrobial lotion soaps may be unknown or proprietary to the manufacturer, the amount (percent by weight) of PCMX in each of the soaps is known and disclosed hereinbelow in Table IV. Moreover, upon examination of the ingredients for the commercial antimicrobial products, it was observed that they all contained at least one of the ingredients tested and found in Table I to inhibit the antimicrobial activity of PCMX.

The two prototype PCMX antimicrobial soap formulations of the present invention are found in Table II as Compositions 4 and 5. These formulations, contain 0.3 percent by weight and 0.5 percent by weight PCMX, respectively, and were formulated using only those ingredients which exhibited no inhibition to PCMX in the ingredient screening process disclosed hereinabove in Table I.

A thirty-second efficacy screen was then conducted using the process detailed hereinabove prior to Table I. Each of the ten commercial antimicrobial soaps and prototype Composition No. 5 were tested against *Staphylococcus aureus* (ATCC Accession No. 33591) and *Escherichia coli* (ATCC Accession No. 8739). Table V reports the antibacterial efficacy in terms of log reduction for a 30 second exposure screen performed against these bacteria and the amount of PCMX in each formulation.

TABLE II

PCMX: PROTOTYPE EFFICACY STUDY
PROTOTYPE FORMULATIONS

| INGREDIENTS {tradename} | PROTOTYPE (PERCENT BY WEIGHT) | | | | | |
|---|---|---|---|---|---|---|
| | 1 | 2 | 3 | 4 | 5 | 6 |
| Para-chloro-meta-xylenol (PCMX) | .3 | .5 | 1 | .3 | .5 | 1 |
| Propylene Glycol-USP | 3 | 3 | 6 | 3 | 3 | 6 |
| Lauramine Oxide (30% active) | 5 | 5 | 7 | 5 | 5 | 7 |
| Hydroxyethyl cellulose {Natrosol 250 HHR} | .7 | .7 | .7 | .7 | .7 | .7 |
| pH | 5.5 | 5.5 | 5.5 | 7 | 7 | 7 |
| Water | balance to provide 100 percent by weight | | | | | |

TABLE III

PCMX/SURFACTANT EFFICACY STUDY
THIRTY SECOND KILL STUDY AGAINST FOUR BACTERIA

| COMPOSITION | BACTERIA--REDUCTION LOG | | | |
|---|---|---|---|---|
| | *Staphylococcus aureus* (33591) | *Escherichia coli* (8739) | *Pseudomonas aeruginosa* (15442) | *Serratia marcescens* (14756) |
| 1 | >5.6580 | >5.3711 | >5.5611 | >5.5024 |
| 2 | >5.6580 | >5.3711 | >5.5611 | >5.5024 |
| 3 | 4.8798 | >5.3711 | >5.5611 | >5.5024 |
| 4 | 4.6021 | — | — | — |
| 5 | 4.3865 | — | — | — |
| 6 | >5.4472 | — | — | — |

TABLE IV

ANTIBACTERIAL EFFICACY SCREEN OF VARIOUS COMMERCIAL ANTIMICROBIAL SKIN CLEANSERS AND ONE PROTOTYPE COMPOSITION THIRTY SECOND EXPOSURE KILL STUDY

| | | LOG REDUCTION | |
|---|---|---|---|
| Compositions | Percent PCMX | Staphylococcus aureus [ATCC #33591] | Escherichia coli [ATCC #8739] |
| 7 | 3 | 0 | 3.48 |
| 8 | 1.25 | .45 | 1.65 |
| 9 | 1 | .94 | >5.28 |
| 10 | 1 | .22 | .60 |
| 11 | 1 | .13 | 0 |
| 12 | .80 | .13 | .23 |
| 13 | .60 | .74 | >5.28 |
| 14 | .60 | .48 | >5.28 |
| 15 | .50 | .17 | 0 |
| 16 | .50 | .31 | 1.01 |
| 5 | .50 | 4.39 | >5.28 |

As can be seen in Table IV, the antibacterial efficacy of the compositions varies widely with the product and does not parallel the percent concentration of PCMX for both challenge bacteria. These results appear to indicate that the antimicrobial efficacies of antimicrobial skin cleansers are highly dependent upon the formula ingredients. Moreover, it appears that the inhibition of PCMX by formula ingredients can negate the effectiveness of even high concentrations (1 to 3 percent by weight) of PCMX.

Continuing, four of the commercial antimicrobial soap products (Compositions 9, 10, 13 and 16) and the two soap prototype formulations of the present invention (Compositions 4 and 5) were selected for more detailed evaluation against the following four challenge bacteria: Staphylococcus aureus (ATCC #33591), Escherichia coli (ATCC#8739) Pseudomonas aeruginosa (ATCC #14756), and Serratia marcescens (ATCC #14756). Each antimicrobial soap was prepared again using the process set forth prior to Table I. However, it is noted that the plates containing Serratia marcescens was incubated at 26° C. for 48 hours rather than 35° C. Moreover, each antimicrobial soap was tested in triplicate for each challenge bacteria and repeated a total of three times for a total of nine replicates. The antibacterial efficacy results of this evaluation are presented in Table V.

bacterial efficacy, showing greater than 5 log reductions for two of the four challenge bacteria. However, the Compositions 5 and 4 of the present invention containing 0.5 percent by weight and 0.3 percent by weight PCMX, respectively, exhibited greater than 5 log reductions for all four challenge bacteria.

Thus, it is believed evident that the in vitro antibacterial efficacies of antimicrobial skin cleansers are highly dependent upon the formula ingredients. Moreover, inhibition of PCMX by formula ingredients can negate the effectiveness of PCMX.

As shown in the Tables, it is apparent that a variety of anionic and nonionic surfactants and emollients can significantly inhibit the efficacy of PCMX in vitro. The extent of the inhibition is dependent upon both the concentration of the ingredient and on the challenge organism. However, the formulations of the present invention which include a substituted phenol, namely PCMX, and a primary surfactant selected from the group consisting of amine oxides, phospholipids, partially neutralized carboxylic acids and diacids, betaines, ethoxylated methylglucosides, and mixtures thereof produce high (>5 Log) reductions of all four challenge bacteria. While antimicrobial Composition 9 yielded moderate to high log reductions for Escherichia coli, Pseudomonas aeruginosa, and Serratia marcescens. All the other commercial antimicrobial products showed very little if any antibacterial efficacy against the methicillin resistant Staphylococcus aureus (Tables IV and V). It is apparent from Table V that the in vitro antibacterial efficacies of the Compositions 5 and 18 (containing 0.5 percent by weight and 0.3 percent by weight PCMX, respectively) far exceed those of the commercial antimicrobial Compositions 9, 10, 13 and 16 (containing 1.0 percent by weight, 1.0 percent by weight, 0.6 percent by weight and 0.5 percent by weight PCMX, respectively).

The studies, which are presented here, clearly demonstrate the effects of the carrier on the active biocide. Although it is tempting to assume that a product containing a high concentration of PCMX is more effective, the in vitro results given clearly demonstrate that this is not true. It is noted that formulation ingredients as well as the concentration of PCMX should be considered in selecting a highly efficacious antimicrobial skin cleanser.

Finally, two additional Compositions (17 and 18) were prepared according to the concepts of the present invention. Each of these compositions are seen as preferred for the present invention. Of course, it will be appreciated that other

TABLE V

ANTIBACTERIAL EFFICACY DATA OF FOUR COMMERCIAL AND TWO PROTOTYPE ANTIMICROBIAL SKIN CLEANSERS

| | | LOG REDUCTION[a] | | | |
|---|---|---|---|---|---|
| Composition | Percent PCMX | Staphylococcus aureus [ATCC #33591] | Escherichia coli [ATCC #8739] | Pseudomonas aeruginosa [ATCC #15442] | Serratia marcescens [ATCC #14756] |
| 9 | 1 | .25 | >5.23 | >5.25 | 2.11 |
| 10 | 1 | .06 | .47 | 3.80 | .07 |
| 13 | .6 | .05 | >5.23 | >5.25 | .57 |
| 16 | .5 | .10 | 1.26 | >5.25 | .14 |
| 5 | .5 | >5.20 | >5.23 | >5.25 | >5.43 |
| 4 | 3 | >5.20 | >5.23 | >5.25 | >5.43 | a = average of 9 replicates

Of the commercial products, Composition 9, containing 1.0 percent by weight PCMX, exhibited the highest antiadditives such as coloring agents, opacifying agents, vitamins or other additives which would not materially affect the composition may be added to these subject compositions without departing from the spirit of the invention. The compositional formulations of each of these compositions are present in Table XII hereinbelow.

TABLE VI

ANTIBACTERIAL EFFICACY SCREEN OF
PCMX ANTIMICROBIAL LOTION SOAP
THIRTY SECOND EXPOSURE KILL STUDY

| INGREDIENTS (tradename) | COMPOSITION (percent by weight) | |
| --- | --- | --- |
| | 17 | 18 |
| Para-Chloro-Meta-Xylenol (PCMX) | .5 | .5 |
| Propylene Glycol USP | 3 | 3 |
| Hydroxyethyl cellulose (Natrosol 250 HHR) | .6 | .6 |
| Disodium ethylenediaminetetraacetic acid ($Na_2EDTA$) | .1 | .1 |
| Cocamine oxide (Mackamine CO) | 4 | 4 |
| Fragrance | .1 | .1 |
| Pearlizing Agent #1 | .5 | — |
| Pearlizing Agent #2 | — | .5 |
| Lactic Acid pH = 6.0 | .23 | .23 |
| Water | balance to provide 100 percent by weight | |

A thirty-second efficacy study was also conducted using the process described hereinabove prior to Table I on these two preferred compositions. Table VII reports the antibacterial efficacy in terms of log reduction for a 30-second exposure screen performed against several challenge bacteria including *Staphylococcus aureus* (ATCC 3591) and *Escherichia coli* (ATCC 8739).

TABLE VII

ANTIBACTERIAL EFFICACY SCREEN OF
PEARLING AGENTS IN PCMX ANTIMICROBIAL
LOTION SOAP
THIRTY SECOND EXPOSURE KILL STUDY

| CHALLENGE MICROBE (ATCC Strain) | COMPOSITION LOG REDUCTION | |
| --- | --- | --- |
| | 17 | 18 |
| *Escherichia coli* (ATCC 8739) | >5.2607 | 5.4255 |
| *Staphylococcus aureus* (ATCC 33591) | 4.4207 | 4.5942 |
| *Staphylococcus aureus* (ATCC 6538) | >5.1319 | — |
| *Serratia marcescens* (ATCC 14756) | >5.5596 | — |
| *Salmonella typhimurium* (ATCC 14028) | >5.2355 | — |
| *Shigella sonnei* (ATCC 11060) | >5.5244 | — |
| *Proteus mirabilis* (ATCC 7002) | >5.5499 | — |
| *Klebsiella ozaenae* (ATCC 11296) | >5.4171 | — |
| *Listeria monocytogenes* (ATCC 7644) | >5.2480 | — |
| *Enterococcus faecium* (ATCC 19434) | >5.1980 | — |
| *Pseudomonas aeruginosa* (ATCC 9027) | >5.3570 | — |
| *Pseudomonas aeruginosa* (ATCC 15442) | >5.5886 | — |
| *Streptococcus pyogenes* (ATCC 19615) | >4.9445 | — |
| *Candida albicans* (ATCC 10231) | 3.6532 | — |

As can be seen, these compositions were highly effective in reducing the colony forming units (cfu's) of the challenged bacteria. Each composition showed at least a 4 log reduction against the bacteria.

Continuing, results of an in vivo glove-juice study performed against *Serratia marcescens* (Accession No. 14756) are presented hereinbelow in Table VIII. In this test, about five milliliters (5 ml) aliquots of approximately $10^8$/ml *Serratia marcescens* were pipetted into each human subject's cupped hands. The inoculum was then distributed evenly over both hands and part of the forearm by gentle massage. After one minute to air dry, the subject's hands were washed with the antimicrobial composition of the present invention and rinsed. Excess water was shaken from the hands and powder-free sterile gloves were placed over the hands. A sterile solution was instilled into each glove, and the wrists of the subject were secured. An attendant massaged the hands through the gloves in a standardized manner for about 60 seconds. Aliquots of the glove juice were removed and serially diluted in a tryptic soy broth (TSB). Duplicate spread plates were prepared from each dilution using tryptic soy agar (TSA). The plates were incubated at 20–25° C. for approximately 48 hours, and plates having 25–250 colony forming units were counted. This procedure was repeated ten times with a minimum of five minutes between applications and washings. The log reduction from the baseline (0 washes) and log bacterial populations after 0, 1, 5 and 10 washes are provided in Table XIII hereinbelow. It can be seen that, based upon the log reduction values obtained for these compositions, the present invention is effective in destroying bacteria and other microorganisms, while at the same time, is mild to the skin.

An additional 15 washes were made to determine the potential for skin irritation. After 25 total washes, skin irritation was found to be negligible.

TABLE VIII

ANTIMICROBIAL LOTION SOAP
0.5% Para-Chloro-Meta-Xylenol

| Subject | Baseline | Wash #1 | Wash #5 | Wash #10 |
| --- | --- | --- | --- | --- |
| 3 | 8.80 | 6.52 | 5.23 | 5.47 |
| 6 | 8.71 | 6.29 | 5.88 | 5.01 |
| 8 | 8.02 | 6.97 | 6.08 | 5.43 |
| Mean $Log_{10}$ Bacterial Populations | 8.51 | 6.59 | 5.73 | 5.30 |
| Mean Log Reduction from Baseline | — | 1.92 | 2.78 | 3.21 |

Thus it should be evident that the compositions of the present invention are highly effective in killing bacteria and other microorganisms while maintaining low skin irritation. The invention is particularly suited for hospital and other health care givers, but is not necessarily limited thereto. The compositions of the present invention can also be used with other surfactants or other ingredients including but not limited to fragrances, chelating and sequestering agents, perfumes, coloring agents, thickeners, antioxidants, emollients, and the like, which do not materially effect the cleansing and disinfecting nature of the composition.

Based upon the foregoing disclosure, it should now be apparent that the use of the composition described herein will carry out the objects set forth hereinabove. It is, therefore, to be understood that any variations evident fall within the scope of the claimed invention and thus, the selection of specific component elements can be determined without departing from the spirit of the invention herein disclosed and described. In particular, primary surfactants according to the present invention are not necessarily limited to those presented in the Examples. Any primary surfactant which, when added to a composition according to the present invention, provides a composition which can be shown to exhibit a log reduction value of at least 3 and preferably at least 5, against *Staphylococcus aureus* is believed suitable for the present invention. Moreover, as noted hereinabove, other viscosifiers and thickeners can be substituted for the hydroxyethyl cellulose. Thus, the scope of the invention shall include all modifications and variations that may fall within the scope of the attached claims.

What is claimed is:

1. An antimicrobial cleansing composition consisting essentially of:
   about 0.1 percent by weight to about 4 percent by weight of 4-chloro-3,5-dimethylphenol; and
   an effective amount of not more than about 20 percent by weight of at least one primary surfactant selected from the group consisting of amine oxides, phospholipids, partially neutralized carboxylic acids and dicarboxylic acids, alkylammonio carboxylates having from 8 to 18 carbon atoms ethoxylated methylglucosides, and mixtures thereof;
   said composition being devoid of any anionic and nonionic surfactants, essentially devoid of any other surfactants, and devoid of alcohol solvents, the balance being water.

2. An antimicrobial cleansing composition, as set forth in claim 1, wherein said at least one primary surfactant is an amine oxide having an alkyl chain length of from about $C_8$ to about $C_{16}$.

3. An antimicrobial cleansing composition, as set forth in claim 1, further consisting essentially of a polymeric viscosifier.

4. An antimicrobial cleansing composition, as set forth in claim 3, wherein said polymeric viscosifier is hydroxyethyl cellulose.

5. An antimicrobial cleansing composition, as set forth in claim 1, further consisting essentially of an acid to adjust the pH of the composition to between 4 and 8.

6. An antimicrobial cleansing composition, as set forth in claim 1, further consisting essentially of at least one additive selected from the group consisting of fragrances, chelating and sequestering agents, perfumes, coloring agents, opacifying agents, pearlizing agents, vitamins, antioxidants, emollients and skin care additives.

7. An antimicrobial cleansing composition, as set forth in claim 1, further consisting essentially of a water softening agent selected from the group consisting of chelating and sequestering agents.

8. An antimicrobial cleansing composition, as set forth in claim 7, wherein said water softening agent is ethylenediaminetetraacetic acid.

9. An antimicrobial cleansing composition consisting essentially of:
   about 0.1 percent by weight to 4 percent by weight of a chlorophenol substituted phenol; and
   an effective amount of not more than about 20 percent by weight of at least one primary surfactant selected from the group consisting of amine oxides, phospholipids, partially neutralized carboxylic acids and dicarboxylic acids, alkylammonio carboxylates having from 8 to 18 carbon atoms, ethoxylated methylglucosides, and mixtures thereof;
   said composition being devoid of any anionic and nonionic surfactants, essentially devoid of any other surfactants, and devoid of alcohol solvents, the balance being water.

10. An antimicrobial cleansing composition, as set forth in claim 9, wherein said at least one primary surfactant is an amine oxide having an alkyl chain length of from about $C_8$ to about $C_{16}$.

11. An antimicrobial cleansing composition, as set forth in claim 10, wherein said amine oxide is selected from the group consisting of alkylamine oxide and amidopropyl amine oxide.

12. An antimicrobial cleansing composition, as set forth in claim 9, further consisting essentially of a polymeric viscosifier.

13. An antimicrobial cleansing composition, as set forth in claim 12, wherein said polymeric viscosifier is hydroxyethyl cellulose.

14. An antimicrobial cleansing composition, as set forth in claim 9, further consisting essentially of an acid to adjust the pH of the composition to between 4 and 8.

15. An antimicrobial cleansing composition, as set forth in claim 14, wherein said acid is selected from the group consisting of lactic acid, citric acid, acetic acid, glycolic acid, and gluconic acid.

16. An antimicrobial cleansing composition, as set forth in claim 9, wherein said at least one primary surfactant is present in an amount ranging from about 1 percent by weight to about 10 percent by weight of the total composition.

17. An antimicrobial cleansing composition, as set forth in claim 9, further consisting essentially of at least one additive selected from the group consisting of fragrances, chelating and sequestering agents, perfumes, coloring agents, opacifying agents, pearlizing agents, vitamins, antioxidants, emollients and skin care additives.

18. An antimicrobial cleansing composition, as set forth in claim 9, further consisting essentially of a water softening agent selected from the group consisting of chelating and sequestering agents.

19. An antimicrobial cleansing composition, as set forth in claim 18, wherein said water softening agent is ethylenediaminetetraacetic acid.

* * * * *

UNITED STATES PATENT AND TRADEMARK OFFICE
CERTIFICATE OF CORRECTION

PATENT NO.   : 5,635,462
DATED        : June 3, 1997
INVENTOR(S)  : Eleanor J. Fendler et al.

It is certified that error appears in the above-indentified patent and that said Letters Patent is hereby corrected as shown below:

In Column 17, line 12, delete "diearboxylic" and insert therefor ---dicarboxylic---; and In Column 17, line 14, insert a comma between "atoms" and "ethoxylated".

Signed and Sealed this

Twenty-sixth Day of August, 1997

Attest:

BRUCE LEHMAN

Attesting Officer

Commissioner of Patents and Trademarks